United States Patent [19]

Buschmann et al.

[11] Patent Number: 4,532,234

[45] Date of Patent: Jul. 30, 1985

[54] NEOPENTYL-PHENETHYLTRIAZOLES, THEIR PREPARATION AND FUNGICIDES CONTAINING THESE COMPOUNDS

[75] Inventors: Ernst Buschmann; Guenter Schulz, both of Ludwigshafen; Gerd Heilen, Speyer; Ernst-Heinrich Pommer, Limburgerhof; Eberhard Ammermann, Ludwigshafen, all of Fed. Rep. of Germany

[73] Assignee: BASF Aktiengesellschaft, Fed. Rep. of Germany

[21] Appl. No.: 530,085

[22] Filed: Sep. 7, 1983

[30] Foreign Application Priority Data

Sep. 7, 1982 [DE] Fed. Rep. of Germany ....... 3233145

[51] Int. Cl.³ ................... A01N 43/64; A01N 55/00; C07D 249/08; C07F 7/18
[52] U.S. Cl. ................................ 514/63; 514/184; 514/383; 548/101; 548/110; 548/262
[58] Field of Search ............... 548/101, 110, 262; 424/269, 245, 185

[56] References Cited

U.S. PATENT DOCUMENTS 4,278,800 7/1981 Rentzea et al. .................. 548/341
4,328,028 5/1982 Rentzea et al. .................. 548/262

FOREIGN PATENT DOCUMENTS 2610022 9/1976 Fed. Rep. of Germany ...... 548/262
2654890 6/1977 Fed. Rep. of Germany ...... 548/262
2634511 2/1978 Fed. Rep. of Germany ...... 548/262
2650831 5/1978 Fed. Rep. of Germany ...... 548/262
2739352 3/1979 Fed. Rep. of Germany ...... 548/262
2842801 4/1980 Fed. Rep. of Germany ...... 548/262
1529818 10/1978 United Kingdom ............... 548/262
1533706 11/1978 United Kingdom ............... 548/262
1533705 11/1978 United Kingdom ............... 548/262

Primary Examiner—Alton D. Rollins
Attorney, Agent, or Firm—Keil & Weinkauf

[57] ABSTRACT

α-Neopentyl-phenethyltriazoles of the formula I

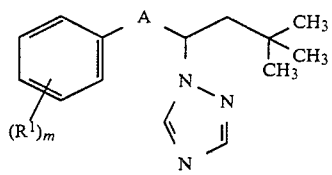

where $R^1$, m and A have the meanings given in the description, processes for their preparation, and their use for controlling fungi.

3 Claims, No Drawings

NEOPENTYL-PHENETHYLTRIAZOLES, THEIR PREPARATION AND FUNGICIDES CONTAINING THESE COMPOUNDS

The present invention relates to novel alpha-neopentyl-phenethyltriazoles, their salts and metal complexes, fungicides which contain these compounds and processes for their preparation.

Triazole derivatives, e.g. compound A, are described in German Laid-Open Application DOS No. 2,739,352.

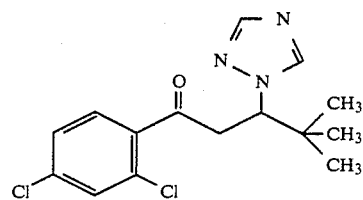

Compounds of this type esssentially exhibit a plant growth-inhibiting action.

It has also been disclosed that the compound 1-(2,4-dichlorophenyl)-3-(1,2,4-triazol-1-yl)-4,4-dimethylpentan-1-ol (B) can be used for regulating plant growth (German Laid-Open Application DOS No. 2,738,725).

Furthermore, it has been disclosed that the compound 1-(2,4-dichlorophenyl)-3-(1,2,4-triazol-1-yl)-4,4-dimethylpentan-1-one-oxime (C) can be used for regulating plant growth (German Laid-Open Application DOS No. 2,842,801).

We have found that alpha-neopentyl-phenethyltriazoles of the formula

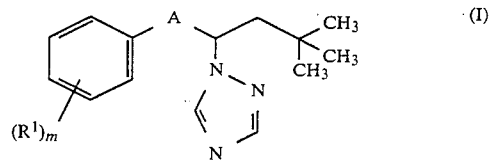

where $R^1$ is alkyl ($C_1$-$C_4$-alkyl), phenyl, $CF_3$, alkoxy ($C_1$-$C_4$-alkoxy) or halogen, m is 0, 1, 2, 3 and A is C=X, CHY or $CR^2R^3$, where X is O or $NOR^4$, Y is $OR^5$, Oacyl ($OC_1$-$C_4$acyl, Obenzoyl) or $OSi(CH_3)_3$, $R^2$ is OH or $OCH_3$, $R^3$ is alkyl ($C_1$-$C_4$-alkyl), aralkyl (benzyl), aryl (phenyl) or vinyl and $R^4$ and $R^5$ are each H, alkyl ($C_1$-$C_6$-alkyl), allyl, propargyl or aralkyl (benzyl), and the plant-tolerated salts and metal complexes of these compounds have a good fungicidal action, which is superior to that of the known triazole derivatives.

$R^1$ is, for example, methyl, ethyl, n-propyl, i-propyl, n-butyl, tert.-butyl, phenyl, $CF_3$, methoxy, ethoxy, isopropoxy, fluorine, chlorine, bromine or iodine.

$R^3$ is, for example, methyl, ethyl, n-propyl, n-butyl, phenyl, 4-$CH_3$-phenyl, 4-Cl-phenyl, 4-Br-phenyl, vinyl, benzyl or 4-Cl-benzyl.

$R^4$ and $R^5$ are, for example, hydrogen, $C_1$-$C_6$-alkyl, methyl, ethyl, propyl, i-propyl, butyl, i-butyl, pentyl, 3,3-dimethylbutyl or hexyl, or benzyl, 4-F-benzyl, 4-$CH_3$-benzyl, allyl or propargyl. Oacyl is, for example, Oacetyl, Opropionyl or Obenzoyl.

Examples of plant-tolerated salts of the compounds are hydrochlorides, hydrobromides, sulfates, phosphates, oxalates, acetates, formates, nitrates and dodecylbenzenesulfonates. Examples of metal complexes are those with copper or zinc.

The novel compounds contain one or two asymmetric carbon atoms and can therefore occur in the form of their optical isomers. The present invention relates both to the pure optical isomers and to mixtures of these.

Scheme 1 shows the preparation of the novel compounds by means of well-known reactions.

Scheme 1

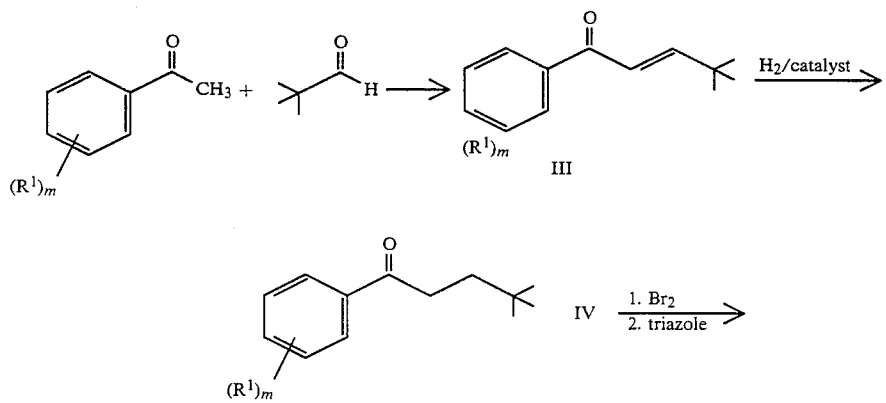

-continued
Scheme 1

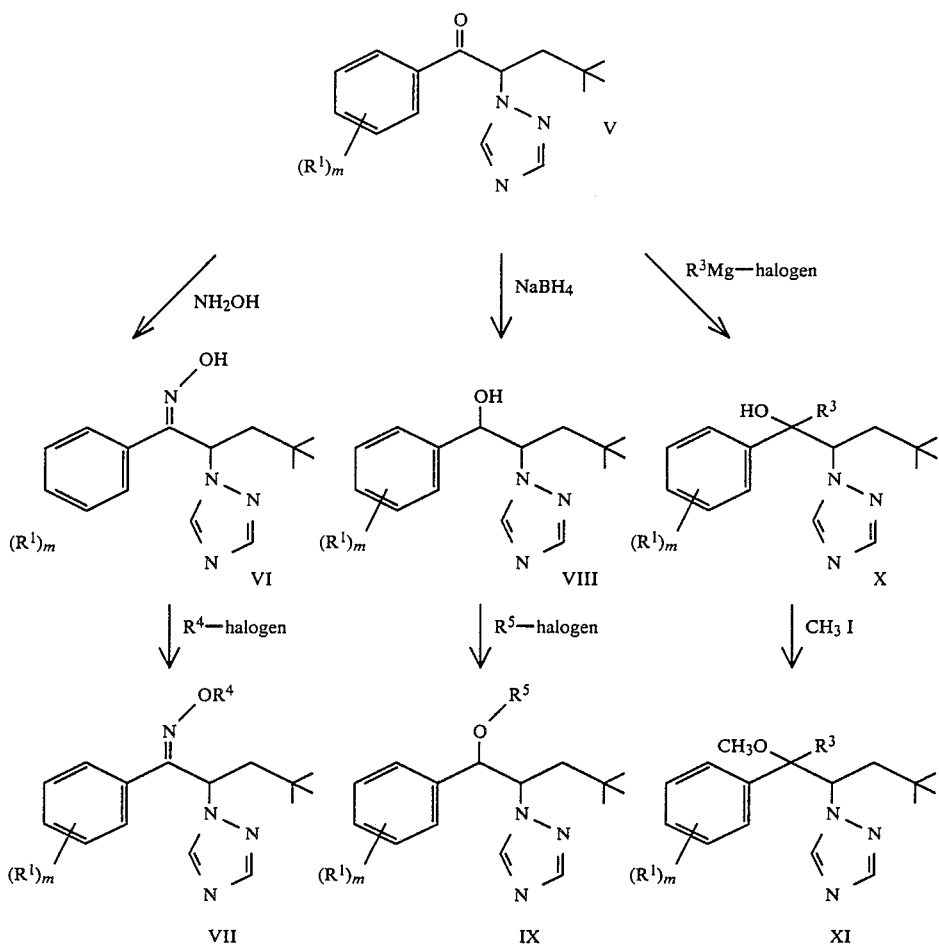

It often proves advantageous to introduce the triazole ring at a later stage in the synthesis, as shown, for example, in Scheme 2:

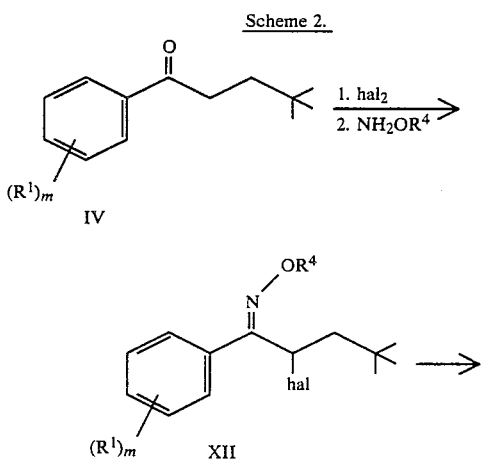

-continued
Scheme 2.

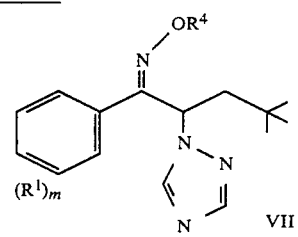

hal = halogen

The process described in Examples 1, 2 and 3 is preferred.

The methods and examples which follow illustrate the preparation of the novel substances:

METHOD 1

Preparation of the α,β-unsaturated ketones (formula III, Scheme 1): eg.

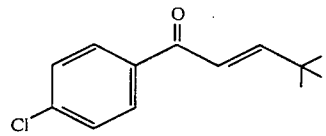

IIIa 430 g of pivalaldehyde in 700 ml of ethanol were added dropwise to a solution of 773 g of 4-chloroacetophenone and 25 g of NaOH in 1400 ml of ethanol at room temperature (20° C.) in the course of 4 hours. Stirring was continued for 1 hour, after which the mixture was neutralized with glacial acetic acid and then evaporated down. The residue was taken up with CH₂Cl₂/H₂O, and the organic phase was washed with water, dried over Na₂SO₄ and evaporated down. Distillation of the residue gave 520 g of the compound IIIa of boiling point 117°–121° C./0.2 mbar.

METHOD 2

Preparation of the dimethylbutyrylbenzenes (formula IV, Schemes 1 and 2): eg.

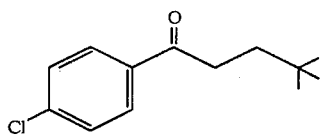

IVa 200 g of IIIa were dissolved in 500 ml of methanol, 20 g of a hydrogenation catalyst (5% of Pr and 0.5% of Pd on Al₂O₃) were added and hydrogenation was then carried out at 130° C. and under 20 bar until the absorption of hydrogen was complete. The catalyst was filtered off, the filtrate was evaporated down and the residue was distilled under reduced pressure to give 165 g of the compound IVa of boiling point 106°–108° C./0.1 mbar.

EXAMPLE 1

Preparation of the α-triazolylketone (formula V, Scheme 1) of the formula

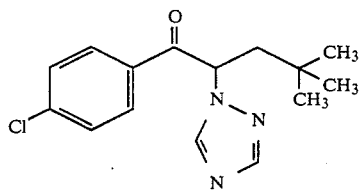

Va (a) 71.2 g of B₂ were added dropwise to a solution of 100 g of the compound IVa in 1 liter of diethyl ether at room temperature (20° C.). Stirring was continued for 1 hour, after which the mixture was poured onto ice water and the ether phase was washed with water, dried with Na₂-SO₄ and evaporated down. The resulting bromoketone was not purified further but was reacted further as follows:

(b) 357 g of the bromoketone obtained as described in (a) were added dropwise to a solution of 162 g of 1,2,4-triazole and 249 g of Na₂CO₃ in 1 liter of ethanol, under reflux. The mixture was refluxed for 3 hours, after which it was evaporated down, the residue was taken up with CH₂Cl₂/H₂O, and the organic phase was washed with water, dried over Na₂SO₄ and evaporated down. Distillation of the residue gave 294 g of the compound Va as a yellowish oil of boiling point 180°–184° C./0.4 mbar (compound No. 1).

The hydrochloride can be precipitated by passing HCl gas into a solution of the triazolylketone V in ether. If concentrated HNO₃ is added to a solution of the triazolylketone in ether, the corresponding nitrate is precipitated.

The following novel α-triazolylketones of the formula V can be prepared as described in the above example:

| No. | R¹ | m | Bp °C./mbar | Mp °C. D = Decomposition |
|---|---|---|---|---|
| 1 | 4-Cl | 1 | 180–184/0.4 | |
| 2 | 2,4-Cl₂ | 2 | 200–205/0.6 | |
| 3 | 4-Cl | 1 | hydrochloride | 130 D |
| 4 | 2,4-Cl₂ | 2 | hydrochloride | 147 D |
| 5 | H | 0 | | |
| 6 | 4-CH₃ | 1 | 166–169/0.3 | |
| 7 | 4-Br | 1 | | |
| 8 | 4-t-Bu | 1 | | |
| 9 | 4-C₆H₅ | 1 | | |
| 10 | 4-CF₃ | 1 | | |
| 11 | 4-OCH₃ | 1 | | |
| 12 | 2,3,4-Cl | 3 | | |

EXAMPLE 2

Preparation of the ketoxime (formula VI, Scheme 1)

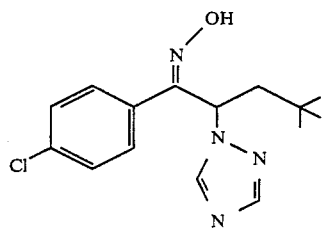

VIa 8.6 g of NH₃⊕OHCl⊖ and 18.6 g of sodium acetate were added to a solution of 37 g of the compound Va in 350 ml of ethanol. The mixture was refluxed for 3 hours, after which it was evaporated down, the residue was taken up with CH₂Cl₂/H₂O, and the organic phase was washed with water, dried over Na₂SO₄ and evaporated down. After trituration with ether, the residue crystallized to give 14 g of compound VIa of melting 136° C. (compound No. 13).

EXAMPLE 3

Preparation of the ketoxime-ether (formula VII, Scheme 1)

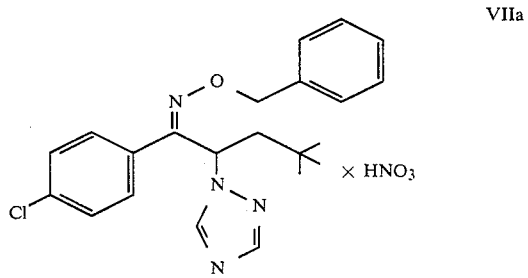

VIIa

A solution of 25.3 g of benzyl chloride in 50 ml of toluene was added dropwise to a mixture of 30.6 g of the oxime VIa, 100 ml of toluene, 12 g of NaOH, 100 ml of H₂O and 1 g of tetrabutylammonium iodide at 80° C. The mixture was stirred for 8 hours at this temperature, after which the organic phase was washed several times with water, dried over Na₂SO₄ and evaporated down. The residue was dissolved in ether, and 10 g of concentrated HNO₃ were added dropwise to the solution while cooling with ice. The nitrate VIIa which crystallized out was filtered off under suction, washed with ether and dried to give a product of melting point 112° C. (decomposition) (compound No. 14).

The following novel α-triazolyloximes and oxime-ethers can be prepared as described in the above example:

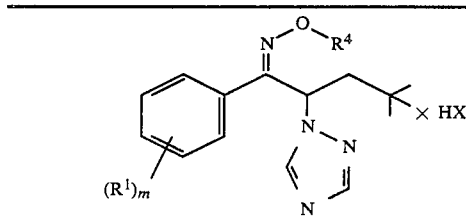

| No. | (R¹)$_m$ | R⁴ | Mp/°C. | HX |
|---|---|---|---|---|
| 13 | 4-Cl | H | 136 | |
| 14 | 4-Cl | CH₂C₆H₅ | 112 D | HNO₃ |
| 15 | 4-Cl | CH₃ | resin | |
| 16 | 4-Cl | CH₃ | 176 D | HCl |
| 17 | 4-Cl | CH₂CH=CH₂ | | |
| 18 | 4-Cl | CH₂—4-Cl—C₆H₄ | | |
| 19 | 2,4-Cl₂ | CH₃ | resin | |
| 20 | 2,4-Cl₂ | CH₃ | 148 D | HNO₃ |
| 21 | 2,4-Cl₂ | CH₂CH=CH₂ | resin | |
| 22 | 2,4-Cl₂ | propargyl | resin | |
| 23 | 2,4-Cl₂ | CH₂C₆H₅ | resin | |
| 24 | 2,4-Cl₂ | CH₂—4-F—C₆H₄ | resin | |
| 25 | 2,4-Cl₂ | CH₂—3-F—C₆H₄ | resin | |
| 26 | 2,4-Cl₂ | CH₂—2-F—C₆H₄ | resin | |
| 27 | 2,4-Cl₂ | CH₂—2,3,6-Cl₃—C₆H₂ | resin | |
| 28 | 2,4-Cl₂ | CH₂—2,6-Cl₂—C₆H₃ | resin | |
| 29 | 2,4-Cl₂ | CH₂—2-I—C₆H₄ | 101–104 | |
| 30 | H | CH₃ | | |
| 31 | 4-C₆H₅ | CH₃ | 149 | |
| 32 | 2,4-Cl₂ | H | resin | |
| 33 | 2,4-Cl₂ | CH₂—2-Cl—6-F—C₆H₃ | resin | |

EXAMPLE 4

Preparation of the triazolylcarbinol (formula VIII, Scheme 1)

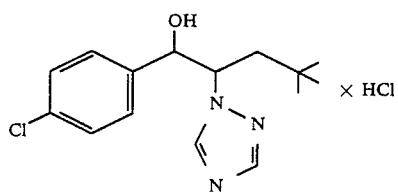

VIIIa 20 g of NaBH₄ were added, a little at a time, to a solution of 35 g of the ketone Va in 200 ml of methanol. The mixture was refluxed for 1 hour and then evaporated down, the residue was boiled for a short time with diluted HCl, and the mixture was rendered alkaline with aqueous NaOH and then extracted with CH₂Cl₂. The organic phase was washed with water, dried over Na₂SO₄ and evaporated down. HCl gas was passed into a solution of the crude product in ether. The precipitated hydrochloride was filtered off under suction, washed with ether and dried to give colorless crystals of melting point 200°–202° C. (decomposition) (compound No. 38). Neutralization of the hydrochloride in methanolic NH₃ solution gave the carbinol VIIIb of boiling point 186°–200° C./0.4 mbar and melting point 126°–128° C.

The following novel triazolyl alcohols of the formula VIII can be prepared as described above:

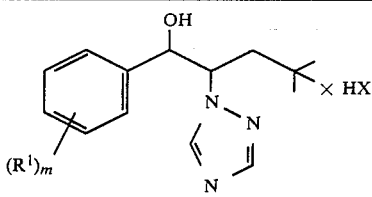

| Nr. | (R¹)$_m$ | HX | Bp. °C./mm Hg | Mp. °C. |
|---|---|---|---|---|
| 38 | 4-Cl | HCl | | 200–202 |
| 34 | 2,4-Cl₂ | | | 160 |
| 35 | H | | | |
| 36 | 4-CH₃ | | 186–192/0,3 | |
| 37 | 4-Br | | | |
| 43 | 4-Cl | | | |
| 39 | 4-C₆H₅ | | | |
| 40 | 4-CF₃ | | | |
| 41 | 4-OCH₃ | | | |
| 42 | 2,3,4-Cl₃ | | | |

EXAMPLE 5

Preparation of the triazolyl ether (formula IX, Scheme 1)

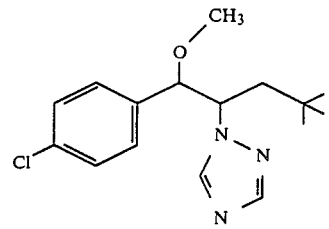

IXa 15.9 g of NaH (80% strength suspension in paraffin) were added, a little at a time, to a solution of 70 g of the carbinol VIIIb and 37.3 g of methyl iodide in 220 ml of dimethylsulfoxide and 770 ml of diethyl ether. When the evolution of H₂ was complete, the mixture was refluxed for half an hour. It was then allowed to cool, 1 liter of ice water was added, the mixture was extracted several times with ether, the organic phase was dried over Na₂SO₄ and evaporated down and the residue was distilled to give 50 g of the compound IXa as a yellowish oil of boiling point 140°–144° C./0.3 mbar (compound No. 56).

The hydrochloride can be precipitated from a solution of the triazolyl ether IXa in n-pentane. Mp. 68° C. (decomposition) (compound No. 44).

The following novel triazolyl ethers of the formula IX can be prepared as described above:

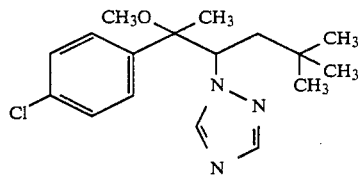

| No. | $(R^1)_m$ | $R^5$ | HX | Mp. °C. Bp. |
|---|---|---|---|---|
| 56 | 4-Cl | $CH_3$ | | 140–144 0.3 mbar |
| 44 | 4-Cl | $CH_3$ | HCl | 68 |
| 45 | 4-Cl | $C_2H_5$ | | 158–166 0.4 mbar |
| 46 | 4-Cl | $CH_2CH=CH_2$ | | 156–167 0.1 mbar |
| 47 | 4-Cl | propargyl | | |
| 48 | 4-Cl | $CH_2C_6H_5$ | | |
| 49 | 2,4-$Cl_2$ | $CH_3$ | | 142–146 0.3 mbar |
| 50 | 2,4-$Cl_2$ | $CH_3$ | HCl | 194 |
| 51 | 2,4-$Cl_2$ | $C_2H_5$ | | 140–148 0.2 mbar |
| 52 | 2,4-$Cl_2$ | $C_2H_5$ | HCl | 162 |
| 53 | H | $CH_3$ | | |
| 54 | 4-Br | $CH_3$ | | |
| 55 | 4-$CF_3$ | $CH_3$ | | |

EXAMPLE 6

Preparation of the triazolylcarbinol (formula X, Scheme 1):

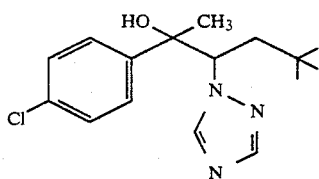

A solution of 50 g of the triazolyl ketone Va in 100 ml of ether was added dropwise to a Grignard compound prepared from 10.3 g of Mg turnings and 61 g of $CH_3I$ in 300 ml of ether. The mixture was refluxed for 2 hours and then hydrolyzed with concentrated aqueous $NH_4Cl$ solution.

The organic phase was washed several times with water, dried over $Na_2SO_4$ and evaporated down. Distillation of the residue gave 39 g of a yellowish resin of boiling point 170°–172° C./0.4 mbar (compound No. 71).

The following novel triazolylcarbinols X can be prepared as described above:

| No. | $(R^1)_m$ | $R^3$ | HX | Mp. °C. Bp. |
|---|---|---|---|---|
| 71 | 4-Cl | $CH_3$ | | 170–172 0.4 mbar |
| 57 | 4-Cl | $CH_2C_6H_5$ | | resin |
| 58 | 4-Cl | $CH=CH_2$ | | resin |
| 59 | 4-Cl | 4-Cl—$C_6H_4$ | | 190 |
| 60 | 4-Cl | n-propyl | | resin |
| 61 | 4-Cl | $C_6H_5$ | $HNO_3$ | 170 D |
| 62 | 4-Cl | $C_2H_5$ | | resin |
| 63 | 2,4-$Cl_2$ | $CH_3$ | | |
| 64 | 2,4-$Cl_2$ | $C_6H_5$ | | 176 |
| 65 | 2,4-$Cl_2$ | $C_2H_5$ | | resin |
| 66 | 2,4-$Cl_2$ | n-propyl | | resin |
| 67 | 2,4-$Cl_2$ | $CH=CH_2$ | | 166–168 0.4 mbar |
| 68 | H | $CH_3$ | | |
| 69 | 4-Br | $CH_3$ | | |
| 70 | 4-$CH_3$ | $CH_3$ | | |

EXAMPLE 7

Preparation of the triazolyl ether (formula XI, Scheme 1):

6.2 g of NaH were added, a little at a time, to a solution of 30.8 g of the carbinol Xa and 18.5 g of iodomethane in 390 ml of diethyl ether and 110 ml of dimethylsulfoxide. When the evolution of $H_2$ was complete, the mixture was refluxed for half an hour. It was then cooled, 600 ml of $H_2O$ were added, the mixture was extracted several times with ether, and the organic phase was dried over $Na_2SO_4$ and evaporated down. Distillation of the residue gave 18 g of a yellowish oil of boiling point 180°–182° C./0.4 mbar (compound No. 77).

The following novel triazolyl ethers XI can be prepared as described above:

| No. | $(R^1)_m$ | HX | Mp. °C. Bp. |
|---|---|---|---|
| 77 | 4-Cl | | 180–182 0.4 mbar |
| 72 | 4-Cl | $HNO_3$ | |
| 73 | 2,4-$Cl_2$ | | |
| 74 | H | | |
| 75 | 4-Br | | |
| 76 | 4-$CH_3$ | | |

EXAMPLE 8

Preparation of the metal complex of the formula

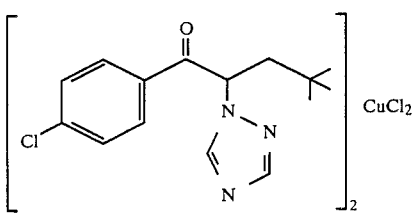

XII

An ethanolic solution of 9 g of CuCl₂.H₂O was combined with a corresponding solution of 23 g of the compound Va, and the mixture was refluxed for a short time. It was then cooled, water was added and the precipitated crude product was triturated with water. The crystalline product was filtered off under suction and dried under reduced pressure to give 15 g of a blue powder of melting point 90° C. (compound No. 78).

EXAMPLE 9

Preparation of the acyloxytriazole of the formula

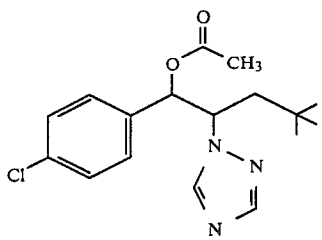

XIIIa 44 g of acetanhydride were added dropwise to a solution of 127 g of the compound (VIIIb), 51 g of pyridine and 0.2 g of 4-dimethylaminopyridine in 1 liter of tetrahydrofuran. The mixture was stirred for 14 hours at room temperature (20° C.) and then evaporated down, the residue was taken up in CH₂Cl₂/H₂O, and the organic phase was washed several times with water, dried over Na₂SO₄ and evaporated down. Distillation of the residue gave 75 g of (XIIIa) as a yellowish oil of boiling point 170°-175° C./0.1 mbar (compound No. 84).

The following novel acyloxy compounds of the formula XIII can be prepared as described above:

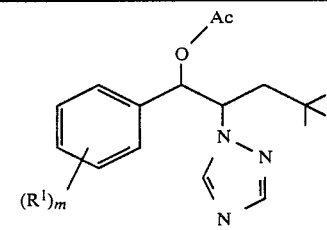

XIII

| No. | (R¹)ₘ | Ac | Bp. °C./mbar |
|---|---|---|---|
| 84 | 4-Cl | acetyl | 170-175 0.1 mbar |
| 79 | 4-Cl | propionyl | |
| 80 | 4-Cl | benzoyl | |
| 81 | 4-Br | acetyl | |
| 82 | 2,4-Cl₂ | acetyl | |
| 83 | 4-CH₃ | acetyl | |

EXAMPLE 10

Preparation of the silyl ether of the formula

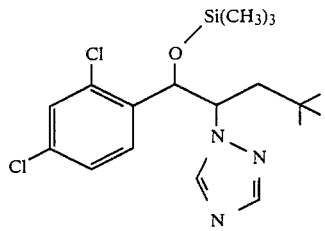

XIVa 20 g of a triazolyl alcohol (compound No. 34) and 17 g of N-trimethylsilylacetamide in 200 ml of toluene were refluxed for 3 hours.

The solution was cooled, washed with water, dried over Na₂SO₄ and evaporated down. The residue obtained comprised 18 g of the compound XIVa in the form of colorless crystals of melting point 67° C. (compound No. 85).

The following silyl ethers of the formula XIV can be prepared as described above:

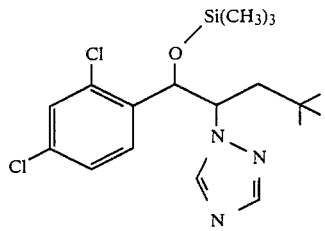

XIV

| No. | (R¹)ₘ | Mp. °C. Bp. |
|---|---|---|
| 89 | 4-Cl | |
| 85 | 2,4-Cl₂ | 67 |
| 86 | 4-CH₃ | |
| 87 | 4-Br | |
| 88 | H | |

The novel compounds, and their salts and metal complex compounds, have an excellent action on a broad spectrum of plant-pathogenic fungi, especially from the Ascomycetes and Basidiomycetes classes. Some of them have a systemic action and may be used as soil and foliar fungicides. They may also be employed for protecting materials, e.g., for combating wood-destroying fungi.

The fungicidal compounds are of particular interest for combating a large number of fungi in various crops or their seed, especially wheat, rye, barley, oats, rice, Indian corn, cotton, soybeans, coffee, sugarcane, fruit, ornamentals in horticulture, and vegetables, such as cucumbers, beans and Cucurbitaceae.

The novel compounds are particularly suitable for combating the following diseases: *Erysiphe graminis* in cereals, *Erysiphe cichoriacearum* in Cucurbitaceae, *Podosphaera leucotricha* in apples, *Uncinula necator* in grapes, *Puccinia* species in cereals, *Rhizoctonia solani* in cotton, *Ustilago* species in cereals and sugarcane, *Venturia inaequalis* (apple scab), *Septoria nodorum* in wheat, *Botrytis cinerea* in grapes and strawberries, *Phytophthora infestans* in potatoes and tomatoes, and *Piricularia oryzae* in rice.

The compounds are applied by spraying or dusting the plants, or treating the seed with the active ingredients. Application may be effected before or after infection of the plants or seed by the fungi.

The novel active ingredients can be converted into the conventional formulations, e.g. solutions, emulsions, suspensions, dusts, powders, pastes and granules. The form of application depends entirely on the purpose for which the agent is to be used; at all events, it should ensure a fine and uniform distribution of the active ingredients. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g. xylene and benzene, chloroaromatics, e.g. chlorobenzene, paraffins, e.g. petroleum fractions, alcohols, e.g. methanol and butanol, amines, e.g. ethanolamine, and dimethylformamide and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The fungicidal agents generally contain from 0.1 to 95, preferably from 0.5 to 90, wt% of active ingredient.

The application rates depend on the effect desired, and range from 0.1 to 3 kg of active ingredient per hectare, or more.

The novel compounds may also be used to protect materials, e.g., to combat wood-destroying fungi such as *Coniophora puteana* and *Polystictus versicolor*. When the active ingredients are used as fungicides for surface coatings and soft PVC, the application rates are from 0.05 to 5% (by weight) of active ingredient, based on the total weight of the paints to be preserved or the PVC to be microbicidally treated. The novel active ingredients may also be used as fungicidally effective components of oily wood preservatives for protecting wood against wood-discoloring fungi. The agents are applied for instance by impregnation or brushing.

The formulations and the ready-to-use products made therefrom, e.g., solutions, emulsions, suspensions, powders, dusts, pastes or granules, are applied in known manner, for example by spraying, atomizing, dusting, scattering, seed-disinfecting, or watering.

I. 20 parts by weight of the compound of Example 1 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in water, a spray liquor is obtained.

II. 3 parts by weight of the compound of Example 2 is intimately mixed with 97 parts by weight of particulate kaolin. A dust is obtained containing 3% by weight of the active ingredient.

III. 30 parts by weight of the compound of Example 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV. 40 parts by weight of the compound of Example 3 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

V. 20 parts of the compound of Example 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

VI. 90 parts by weight of the compound of Example 1 is mixed with 10 parts by weight of N-methyl-alpha-pyrrolidone. A solution is obtained which is suitable for application in the form of very fine drops.

VII. 20 parts by weight of the compound of Example 3 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

VIII. 20 parts by weight of the compound of Example 2 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into water and finely distributing it therein, an aqueous dispersion is obtained.

IX. 10 parts by weight of the compound of Example 3, 20 parts by weight of polyoxyethylene sorbitan monolaurate, 20 parts by weight of methanol and 50 parts by weight of water are stirred to give a solution containing 10 wt% of the active ingredient. More dilute solutions may be prepared by adding water.

In these application forms, the agents according to the invention may also be mixed and applied with other active ingredients, e.g, herbicides, insecticides, growth regulators, other fungicides and fertizilizers. When mixed with other fungicides, the spectrum of fungicidal action is in many cases increased.

Examples of fungicides which may be combined with the active ingredients according to the invention are as follows:
sulfur
dithiocarbamates and derivatives thereof, such as
ferric dimethyldithiocarbamate
zinc dimethyldithiocarbamate
manganese ethylenebisdithiocarbamate
zinc ethylenebisthiocarbamate
tetramethylthiuram disulfide
manganese-zinc ethylenediamine-bisdithiocarbamate
zinc-(N,N'-propylene-bisdithiocarbamate)
ammonia complex of zinc-(N,N'-ethylene)-bisdithiocarbamate
and
N,N'-polyethylene-bis-(thiocarbamoyl)-disulfide
ammonia complex of zinc-(N,N'-propylene-bisdithiocarbamate)
and
N,N'-polypropylene-bis-(thiocarbamoyl)-disulfide
nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
diisopropyl 5-nitroisophthalate
heterocyclic structures, such as 2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl]-3-phenyl-1,2,4-triazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxycarbonylaminobenzimidazole
2-[furyl-(2)]-benzimidazole
2-[thiazolyl-(4)]-benzimidazole
N-(1,1,2,2-tetrachloroethylthio)-tetrahydrophthalimide
N-trichloromethylthiotetrahydrophthalimide
N-trichloromethylthiophthalimide
N-dichlorofluoromethylthio-N',N'-dimethyl-N-phenyl-sulfuric acid diamide
5-ethoxy-3-trichloromethyl-1,2,3-thiadiazole
2-thiocyanomethylthiobenzthiazole
1,4-dichloro-2,5-dimethoxybenzole
4-(2-chlorophenylhydrazono)-3-methyl-5-isoxazolone
pyridine-2-thio-1-oxide
8-hydroxyquinoline and its copper salt
2,3-dihydro-5-carboxanilido-6-methyl-1,4-oxathiin
2,3-dihydro-5-carboxanilido-6-methyl-1,4-oxathiin-4,4-dioxide
2-methyl-5,6-dihydro-4-H-pyran-3-carboxanilide
2-methyl-furan-3-carboxanilide
2,5-dimethyl-furan-3-carboxanilide
2,4,5-trimethyl-furan-3-carboxanilide
2,5-dimethyl-furan-3-carboxylic acid cyclohexylamide
N-cyclohexyl-N-methoxy-2,5-dimethyl-furan-3-carboxamide
2-methyl-benzoic acid anilide
2-iodobenzoic anilide
N-formyl-N-morpholine-2,2,2-trichloroethylacetal
piperazine-1,4-diylbis-(1-(2,2,2-trichloroethyl)-formamide
1-(3,4-dichloroanilino)-1-formylamino-2,2,2-trichloroethane
2,6-dimethyl-N-tridecyl-morpholine and its salts 2,6-dimethyl-N-cyclododecyl-morpholine and its salts
N-[3-(p-tert.-butylphenyl)-2-methylpropyl]-cis-2,6-dimethylmorpholine
N-[3-(p-tert.-butylphenyl)-2-methylpropyl]-piperidine
1-[2-(2,4-dichlorophenyl)-4-ethyl-1,3-dioxolan-2-yl-ethyl]-1-H-1,2,4-triazole
1-[2-(2,4-dichlorophenyl)-4-n-propyl-1,3-dioxolan-2-yl-ethyl]-1-H-1,2,4-triazole
N-(n-propyl)-N-(2,4,6-trichlorophenoxyethyl)-N'-imidazol-ylurea
1-(4-chlorophenoxy)-3,3-dimethyl-1-(1H-1,2,4-triazol-1-yl)-2-butanone
1-(4-chlorophenoxy)-3,3-dimethyl-1-(1H-1,2,4-triazol-1-yl)-2-butanol
alpha-(2-chlorophenyl)-alpha-(4-chlorophenyl)-5-pyrimidin-methanol
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl-2-thioureido)-benzene
and various substances, such as
dodecylguanidine acetate
3-[2-(3,5-dimethyl-2-oxycyclohexyl)-2-hydroxyethyl]-glutarimide
hexachlorobenzene
D,L-methyl-N-(2,6-dimethylphenyl)-N-(2-furoyl)-alanate
methyl D,L-N-(2,6-dimethylphenyl)-N-(2-methoxyacetyl)-alanate
N-(2,6-dimethylphenyl)-N-chloroacetyl-D,L-2-aminobutyrolactone
methyl DL-N-(2,6-dimethylphenyl)-N-(phenylacetyl)-alanate
5-methyl-5-vinyl-3-(3,5-dichlorophenyl)-2,4-dioxo-1,3-oxazolidine
3-(3,5-dichlorophenyl)-5-methyl-5-methoxymethyl-1,3-oxazolidin-2,4-dione
3-(3,5-dichlorophenyl)-1-isopropyl-carbamoylhydantoin
N-(3,5-dichlorophenyl)-1,2-dimethyl-cyclopropane-1,2-dicarboximide
2-cyano-N-((ethylaminocarbonyl)-2-methoximino)-acetamide.

The following experiments illustrate the biological action of the novel compounds. The following prior art active ingredients were used for comparison purposes:
1-(2,4-dichlorophenyl)-3-(1,2,4-triazol-1-yl)-4,4-dimethylpentan-1-one (A) (German Laid-Open Application DE-OS 2,739,352)
1-(2,4-dichlorophenyl)-3-(1,2,4-triazol-1-yl)-4,4-dimethylpentan-1-ol (B) (German Laid-Open Application DE-OS 2,738,725)
1-(2,4-dichlorophenyl)-3-(1,2,4-triazol-1-yl)-4,4-dimethylpentan-1-one oxime (C) (German Laid-Open Application DE-OS 2,842,801).

EXPERIMENT 1

Action on wheat mildew

Leaves of pot-grown wheat seedlings of the "Jubilar" variety were sprayed with aqueous liquors, the solids of which consisted of 80% (by weight) of active ingredient and 20% of emulsifier, and dusted, 24 hours after the sprayed-on layer had dried, with spores of wheat mildew (*Erysiphe graminis* var. tritici). The plants were then placed in a greenhouse at 20° to 22° C. and 75 to 80% relative humidity. The extent of mildew spread was determined after 7 days.

The results of this experiment show that for instance compounds nos. 1, 2, 3, 14, 15, 16, 19, 21, 31, 38, 48, 49, 51, 57, 60, 61, 62, 65, 66 and 85, applied as 0.05, 0.025, 0.006 and 0.0015 wt% sprays, had a better fungicidal action (97%) than the prior art compounds A and C (50%).

EXPERIMENT 2

Action on leaf rust of wheat

Leaves of pot-grown wheat seedlings of the "Jubilar" variety were dusted with spores of rust (*Puccinia recondita*). The pots were then placed in a high humidity (90-95%) chamber at from 20° to 22° C. for 24 hours. During this time, the spores germinated and the germ tubes penetrated into the leaf tissue. The infected plants were then sprayed to run-off with aqueous liquors, the solids comprising 80% of active ingredient and 20% of emulsifier. After the spray coating had dried, the test plants were set up in a greenhouse at from 20° to 22° C. and from 65 to 70% relative humidity. After 8 days, the degree of development of the rust fungi on the leaves was determined.

In this experiment, for instance compounds nos. 1, 2, 3, 14, 15, 16, 31, 57, 58, 65, 67 and 77, applied as 0.05 or 0.025 sprays, had a better fungicidal action (97%) than prior art compounds A, B and C (0%).

EXPERIMENT 3

Action on barley mildew

Leaves of pot-grown barley seedlings of the "Asse" variety were sprayed with aqueous liquors, the solids comprising 80% of active ingredient and 20% of emulsifier, and, after 24 hours, dusted with spores of barley mildew (*Erysiphe graminis* spp. hordei). The plants were then set up in the greenhouse at from 20° to 22° C. and a relative humidity of from 75 to 80%. After 7 days, the degree of fungus spread was ascertained.

The results show that for example compounds nos. 3, 14, 15, 16, 19, 20, 34, 38, 43, 44, 49, 51, 52, 56, 57, 60, 61, 66, 67, 77 and 85, applied as 0.05, 0.006 and 0.0015% spray liquors, had a better fungicidal action (97%) than prior art compounds A, B and C (60%).

EXPERIMENT 4

Action on *Botrytis cinerea* in pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidal suspension of the fungus *Botrytis cinerea,* and placed at 22° to 24° C. in a chamber of high humidity. After 5 days, the disease had spread to such a great extent on the untreated plants that the necroses covered the major portion of the leaves.

In this experiment, for instance compounds nos. 2, 15, 19, 29, 31, 57, 58, 61, 67 and 77, applied as 0.05% sprays, had a good fungicidal action (97%).

We claim:

1. An alpha-neopentyl-phenethyltriazole of the formula

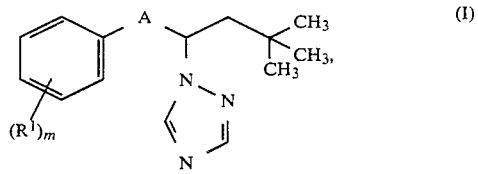

where $R^1$ is $C_1$–$C_4$ alkyl, phenyl, $CF_3$, $C_1$–$C_4$ alkoxy or halogen, m is 0, 1, 2, 3 and A is C=X, CHY or $CR^2R^3$, where X is O or $NOR^4$, Y is $OR^5$, O-acetyl, O-propionyl, or O-benzoyl or $OSi(CH_3)_3$, $R^2$ is OH or $OCH_3$, $R^3$ is $C_1$–$C_4$ alkyl, phenyl, 4-$CH_3$-phenyl, 4-Cl-phenyl, 4-Br-phenyl, vinyl, benzyl or 4-Cl-benzyl and $R^4$ and $R^5$ are each H, $C_1$–$C_6$ alkyl benzyl, 4-F-benzyl, 4-$CH_3$-benzyl, allyl or propargyl or a plant-tolerated salt or metal complex thereof.

2. A fungicide containing a fungicidally effective amount of a compound of the formula I as set forth in claim 4 and a solid or liquid carrier.

3. A process for combating fungi, wherein a fungicidally effective amount of a compound of the formula I is set forth in claim 1 is allowed to act on the fungi themselves, or on materials, plants or seed threatened by fungus attack.

* * * * *